United States Patent [19]
Allen et al.

[11] Patent Number: 5,354,304
[45] Date of Patent: Oct. 11, 1994

[54] MODULAR LIGATION CLIP APPLICATOR

[75] Inventors: William J. Allen, Stratford; George Jessup, Brookfield; Frederick F. Ahari, Southport, all of Conn.; Lawrence Crainich, Charlestown, N.H.

[73] Assignee: American Cyanamid Co., Wayne, N.J.

[21] Appl. No.: 960,080

[22] Filed: Oct. 13, 1992

[51] Int. Cl.$^5$ .............................................. A61B 17/00
[52] U.S. Cl. ................................... 606/142; 606/139; 606/151; 227/901
[58] Field of Search ............... 606/139, 142, 143, 151; 227/901, 19, 175

[56] References Cited

U.S. PATENT DOCUMENTS

| | | |
|---|---|---|
| 3,631,707 | 1/1972 | Miller . |
| 3,675,688 | 6/1972 | Bryan et al. ......................... 606/143 |
| 3,777,538 | 12/1973 | Weatherby et al. . |
| 3,882,854 | 5/1975 | Hulka et al. ......................... 606/142 |
| 4,064,881 | 12/1977 | Meredith ............................. 606/142 |
| 4,169,476 | 10/1979 | Hiltebrandt ......................... 606/142 |
| 5,100,416 | 3/1992 | Oh et al. ............................. 606/142 |

FOREIGN PATENT DOCUMENTS

| | | |
|---|---|---|
| 0409569 | 1/1991 | European Pat. Off. ............ 606/142 |
| 2180455 | 4/1987 | United Kingdom ................ 606/142 |
| WO/91/087-08 | 6/1991 | World Int. Prop. O. .......... 606/139 |

Primary Examiner—Stephen C. Pellegrino
Assistant Examiner—Jeffrey A. Schmidt
Attorney, Agent, or Firm—Charles F. Costello, Jr.

[57] ABSTRACT

A two-part ligation clip applicator comprises a handle assembly having a squeezable trigger and an elongated shaft connected at its proximal end to the handle assembly. The elongated shaft houses a sliding advancer which is actuated by squeezing the trigger to move axially in a forward direction in the shaft. In addition, a module is mountable at a distal end of the elongated shaft and supports a ligation clip. The module has a cartridge housing, latches pivotably mounted within the housing for gripping first part of the ligation clip, and a sliding pusher slidable within the housing by actuation of the advancer to engage the second part of the ligation clip and advance it relative to the first part to close the first part.

23 Claims, 9 Drawing Sheets

FIG. 10

MODULAR LIGATION CLIP APPLICATOR

BACKGROUND OF THE INVENTION

1. Field of the Invention

The present invention relates generally to a medical instrument for use with a surgical ligation clip. More particularly, the invention is directed to a modular applicator for positioning, securing, and closing the surgical ligation clip around a vessel to be occluded.

A surgical ligation clip is used to compress a severed blood vessel to stop the flow of blood. The modular applicator of the subject invention is particularly designed for use preferably with a two-part surgical ligation clip. The first part comprises generally a Y-shaped clamp or track having two extended arms for fitting around a vessel to be ligated. The second part is a U-shaped clip body with an extended slot for slidably engaging the track and closing the arms about the vessel. Ligation clips of this type are disclosed in U.S. Pat. No. 4,590,937 and in U.S. patent application Ser. No. 07/906,938, filed Jun. 30, 1992, both of which are assigned to the assignee of the subject invention and are incorporated herein by reference.

2. Description of the Prior Art

There are many types of known mechanical applicators for closing a conventional ligation clip around a vessel. Several examples of known applicators include the so-called push-pull type, which uses a plunger or a piston, or a fulcrum type applicator having a scissors-like or pliers-like handle.

Other examples of devices for applying metal ligation clips that include movable jaws which close together to crimp the clip about a vessel are disclosed in U.S. Pat. Nos. 4,576,166; 4,662,373; and 4,598,711, each of which is assigned to the assignee of the present invention, as well as in U.S. Pat. Nos. 4,152,920; 4,242,902; 5,084,057; and 5,100,420.

However, further improvements for applying a surgical ligation clip are desirable, and in particular, a ligation clip applicator is beneficial for use with unique two-part ligation clips such as are disclosed in U.S. Pat. No. 4,590,937 and in U.S. patent application Ser. No. 07/906,938. Those ligation clips provide many advantages over known metal clips since they provide superior clamping strength and may be made of bioabsorbable materials.

SUMMARY OF THE INVENTION

Accordingly, it is a general object of the present invention to provide an improved ligation clip applicator.

It is another object of the present invention to provide a ligation clip applicator for use with a two-part ligation clip, and more particularly, two-part ligation clips of the type disclosed in U.S. Pat. No. 4,590,937 and U.S. patent application Ser. No. 07/906,938.

It is another object of the present invention to provide a ligation clip applicator that can apply a ligation clip using minimally invasive surgery.

It is still another object of the present invention to provide a ligation clip applicator that can be used proficiently to manipulate a mounted ligation clip and place it in position about the vessel to be ligated.

In accordance with one aspect of the invention, a ligation clip applicator comprises a module for supporting a ligation clip, the module including holding means for holding a first part of the ligation clip in a stationary position and sliding means for advancing another part of the ligation clip forwardly about the first part, and actuation means, connected to the module, for actuating the sliding means.

In accordance with another aspect of the invention, a ligation clip applicator comprises an elongated hollow shaft housing a sliding advancer, and a handle assembly connected to a proximal end of the shaft and having actuating means for actuating the sliding advancer. A module is connected to a distal end of the shaft and includes holding means for holding a first part of the ligation clip in a stationary position and sliding means for advancing another part of the ligation clip forwardly about the first part.

In accordance with yet another aspect of the invention, a ligation clip applicator comprises a handle assembly having a squeezable trigger and an elongated shaft connected at its proximal end to the handle assembly. The elongated shaft houses a sliding advancer that is actuated by squeezing the trigger to move in the longitudinal direction of the shaft. In addition, a module is connected to a distal end of the elongated shaft for supporting a ligation clip. The module has a cartridge housing, pivotable latches mounted within the housing and a sliding pusher slidable within the housing by actuation of the advancer.

In accordance with yet another aspect of the invention, a module for mounting a two-part ligation clip comprises a cartridge housing, holding means housed in the cartridge housing for holding a first part of the ligation clip in a stationary position, and sliding means, also housed in the cartridge housing, for advancing a second part of the ligation clip about the first part.

The subject invention thus provides a module for mounting the ligation clip onto the applicator. The module is preferably made primarily of plastic or other low cost material and is disposable. In addition, different size modules for mounting various size ligation clips can be interchangeably connected to the same, reusable applicator. The module is connected to a slender, elongated hollow shaft that houses a slidable advancer. A handle assembly connected to the other end of the shaft actuates the advancer to slide it axially within the shaft and abut a pusher disposed in the module. The module holds the clamp of the ligation clip in a stationary position as the advancing pusher moves the sliding clip body forwardly to compress the clamp around the vessel.

These and other objects, aspects, features and advantages of the present invention will become apparent from the following detailed description of the preferred embodiments taken in conjunction with the accompanying drawings.

DESCRIPTION OF THE PREFERRED EMBODIMENTS

For ease of reference, as used herein the term "distal" will refer to that part of the device which is farthest from the surgeon-user, and the term "proximal" refers to that part of the device which is closest to the surgeon-user.

As noted above, the ligation clip applicator of the present invention is specifically designed to apply a two-part ligation clip of the types described in U.S. Pat. No. 4,590,937 and U.S. patent application Ser. No. 07/906,938, both of which are incorporated wherein by reference. For convenience, however, the invention will be described with reference to the two-part ligation clip described in U.S. patent application Ser. No. 07/906,938.

Figure 1:
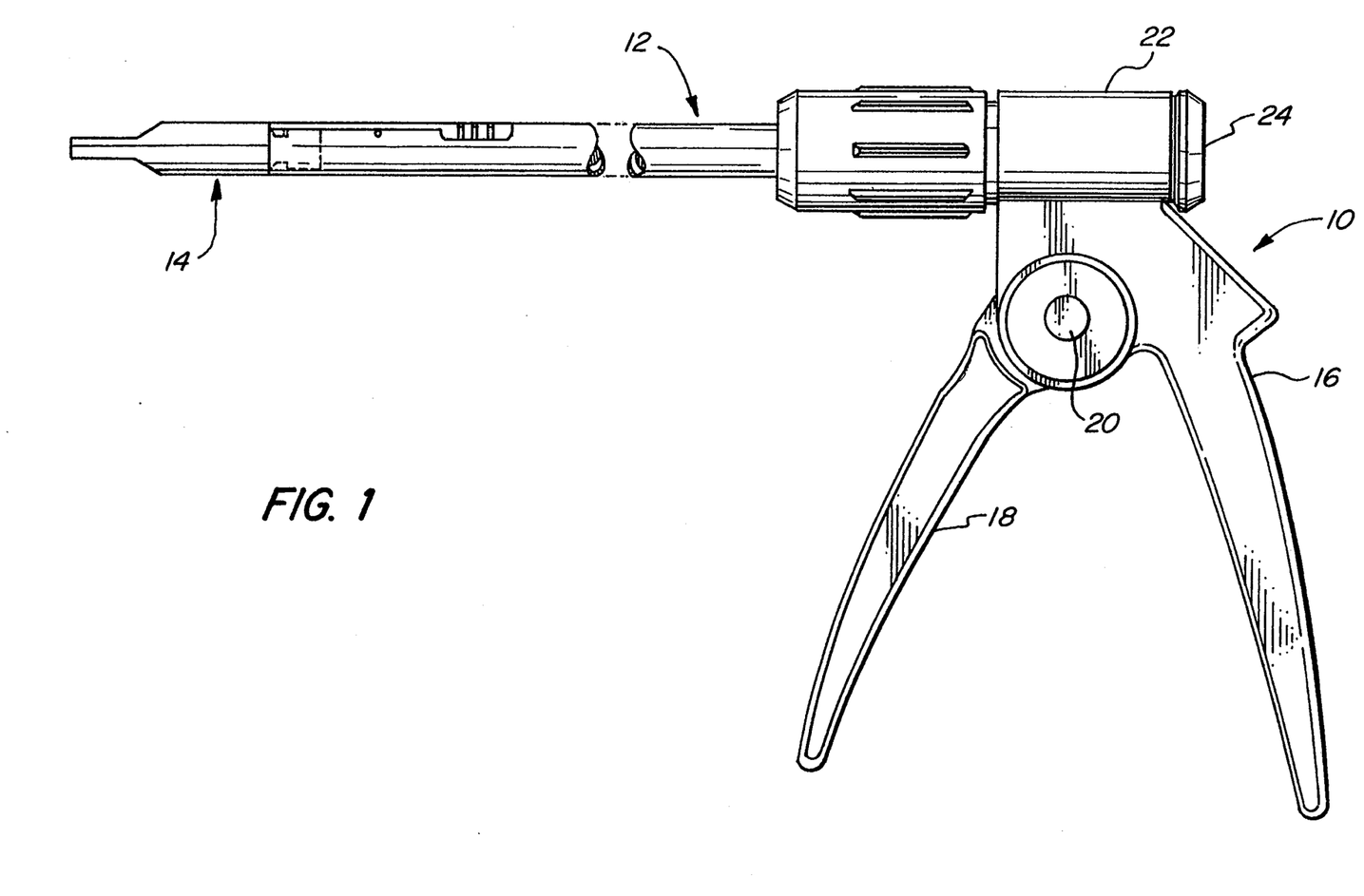
FIG. 1 is a side elevational view of the ligation clip applicator in accordance with the present invention.

The ligation clip applicator of the present invention is shown in FIG. 1 to comprise a handle assembly 10, an elongated and round or cylindrical neck portion 12 projecting from the handle assembly, and a ligation clip module 14 that can be mounted on the end of each neck position. Generally speaking, the ligation clip is loaded into module 14 in a manner that will be described in more detail below and handle assembly 10 is actuated to close, or compress, a first part of the ligation clip around a vessel to be ligated.

Figure 2:
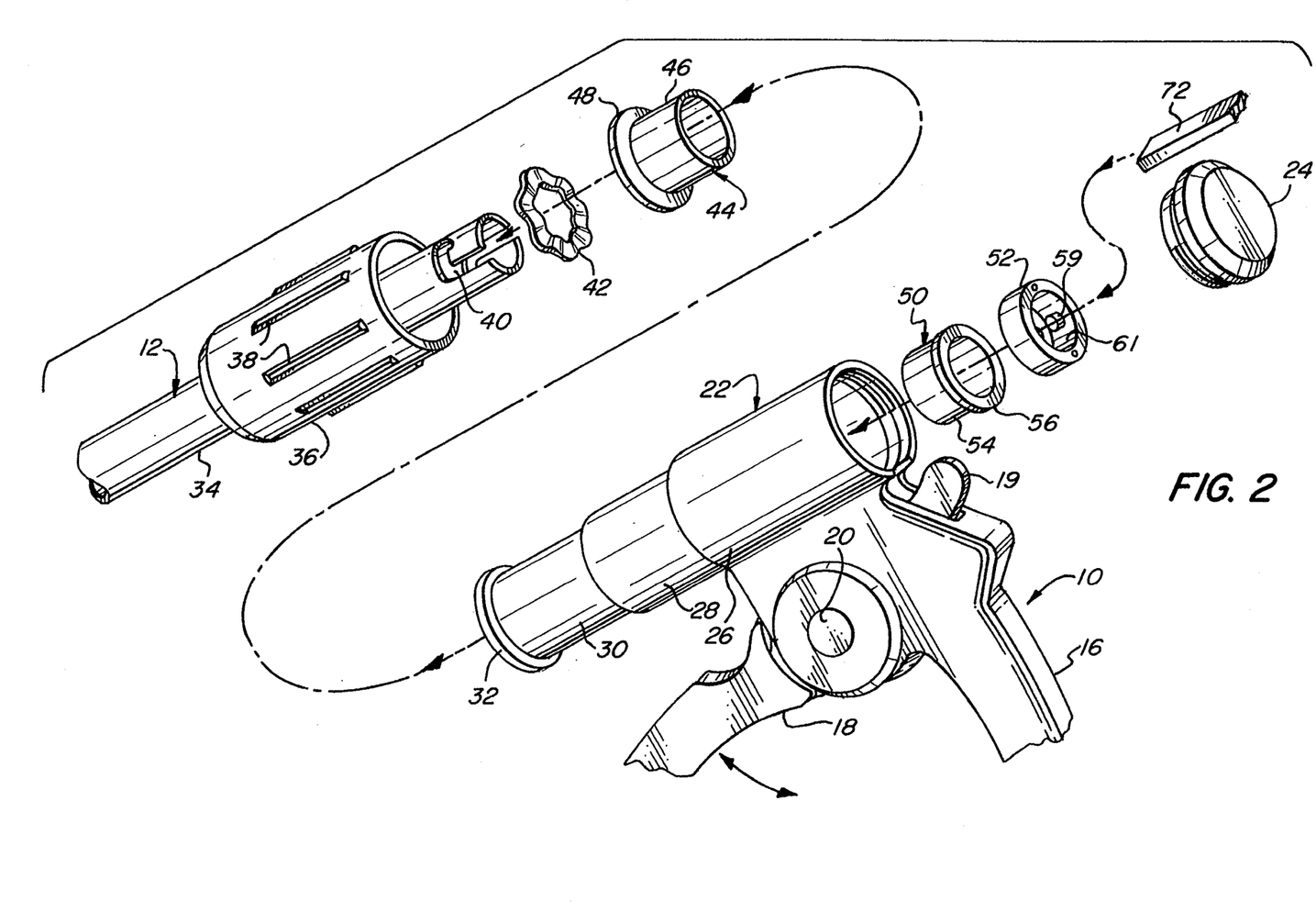
FIG. 2 is an exploded perspective view of a handle assembly and a proximal end of a neck portion of the ligation clip applicator.

The handle assembly as shown in FIG. 1 includes a handle 16 and a squeezable trigger 18 pivotally attached to the handle at pivot shaft 20. A barrel assembly 22 receives the proximal end of the neck portion 12. A threaded end cap 24 closes the proximal end of the barrel. As shown in FIG. 2, the barrel assembly 22 is formed of a first barrel 26, a second barrel 28 and a third barrel 30 of progressively smaller diameters, that together form a telescope-like appearing structure. The smallest diameter barrel, third barrel 30, includes a radially projecting lip 32 at its distal end. The top or actuating end 19 of trigger 18 can also be seen in FIG. 2.

The proximal end of the elongated neck portion shown in FIG. 2 includes a hollow tube or shaft 34 and a collar 36 secured thereto and open at its proximal end. The shaft and collar, as well as the entire handle assembly, are preferably made of high grade surgical steel, such as, for example, stainless steel. The collar includes longitudinal ridges 38 so that it can be gripped easily to rotate the hollow shaft 34 about its longitudinal axis. The proximal end of the hollow shaft has two oppositely disposed J-shaped notches 40, commonly known as "bayonet locks", to secure the shaft in the handle assembly for such rotation in the manner described below.

To assemble the neck portion and handle assembly, a resilient wave washer 42 and a first bushing 44 are placed over the proximal end of hollow shaft 34. The first bushing has a cylindrical portion 46 and a radially projecting rim 48 at its distal end. The hollow shaft is inserted into the open distal end of the barrel assembly 22 until the rim 48 on the first bushing 44 abuts the circumferential lip 32 on third barrel 30 as can be seen in detail in FIG. 5. A second bushing 50 having a cylindrical portion 54 and a circumferential rim 56, and bayonet ring lock 52 are inserted into the open proximal end of the barrel assembly and over the end of the hollow shaft.

Figure 5:
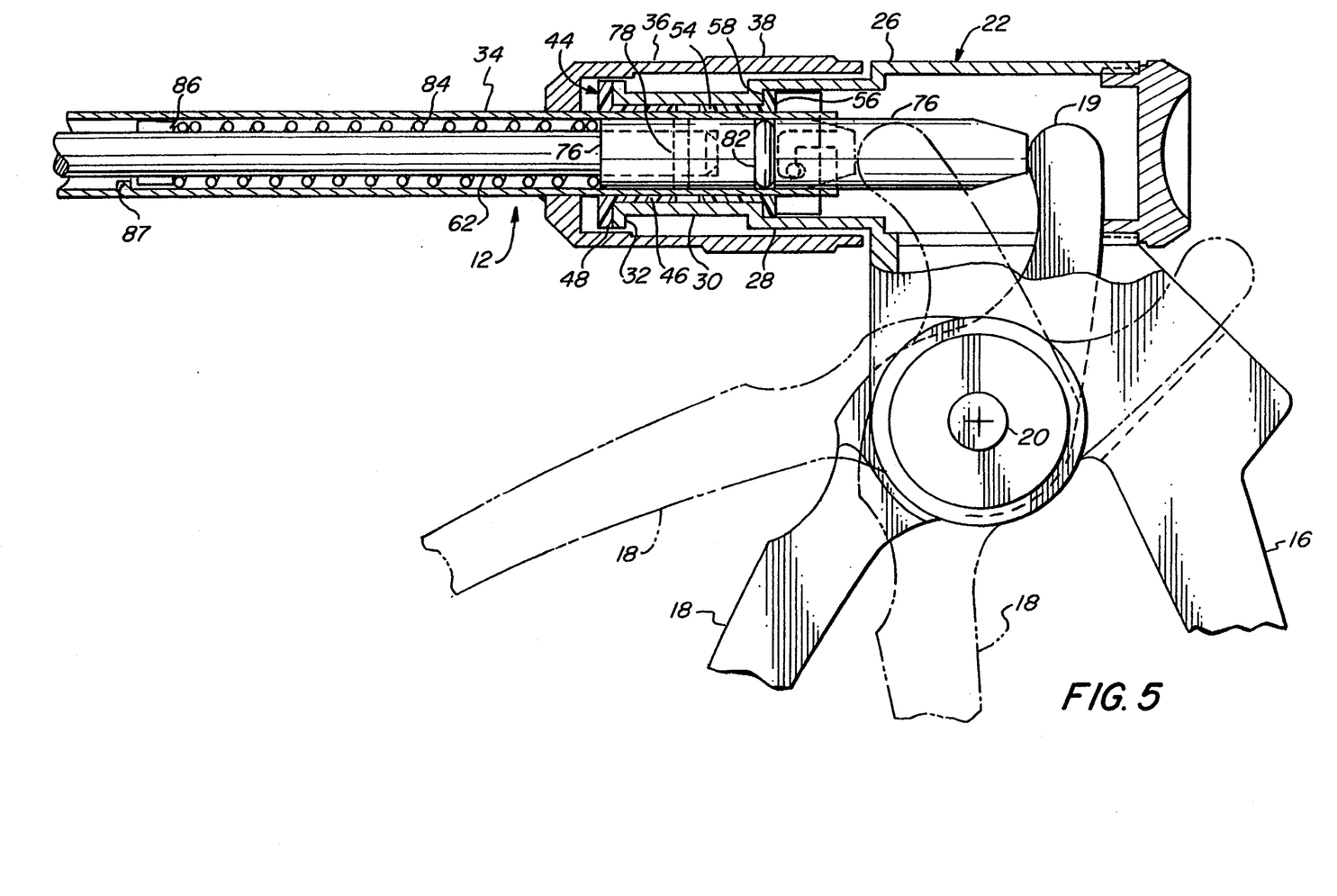
FIG. 5 is a vertical cross-sectional view of the proximal end of the ligation clip applicator showing the handle assembly in three different positions.

Referring again to FIG. 5, the second bushing is inserted until rim 56 abuts a radially projecting ridge 58 formed between the second and third barrels. As best seen in FIG. 2, the bayonet ring lock includes two pins 59 protruding inwardly from its inner cylindrical surface 61. The pins are designed to fit into the J-shaped notches 40 and lock the elongated neck portion in the handle assembly as shown in FIG. 5.

In assembly the hollow shaft 34 and bayonet ring lock 52 are manipulated to guide the pins along the straight section of the J-shaped grooves. When the pins reach the end of the straight portion the hollow shaft is rotated relative to the bayonet ring lock and then moved in a reverse axial direction thereto to position the pins in the tip, or toe, section of the J-shaped grooves and lock the hollow shaft in the handle assembly. The resilient wave washer 42 is compressed between the inner radially projecting proximal surface of the collar 36 and the distal surface of the rim 48 to urge the neck portion assembly forwardly. As will be appreciated, with this assembly the neck portion is freely rotatable about its longitudinal axis while being secured to the handle assembly.

Figures 3, 4:
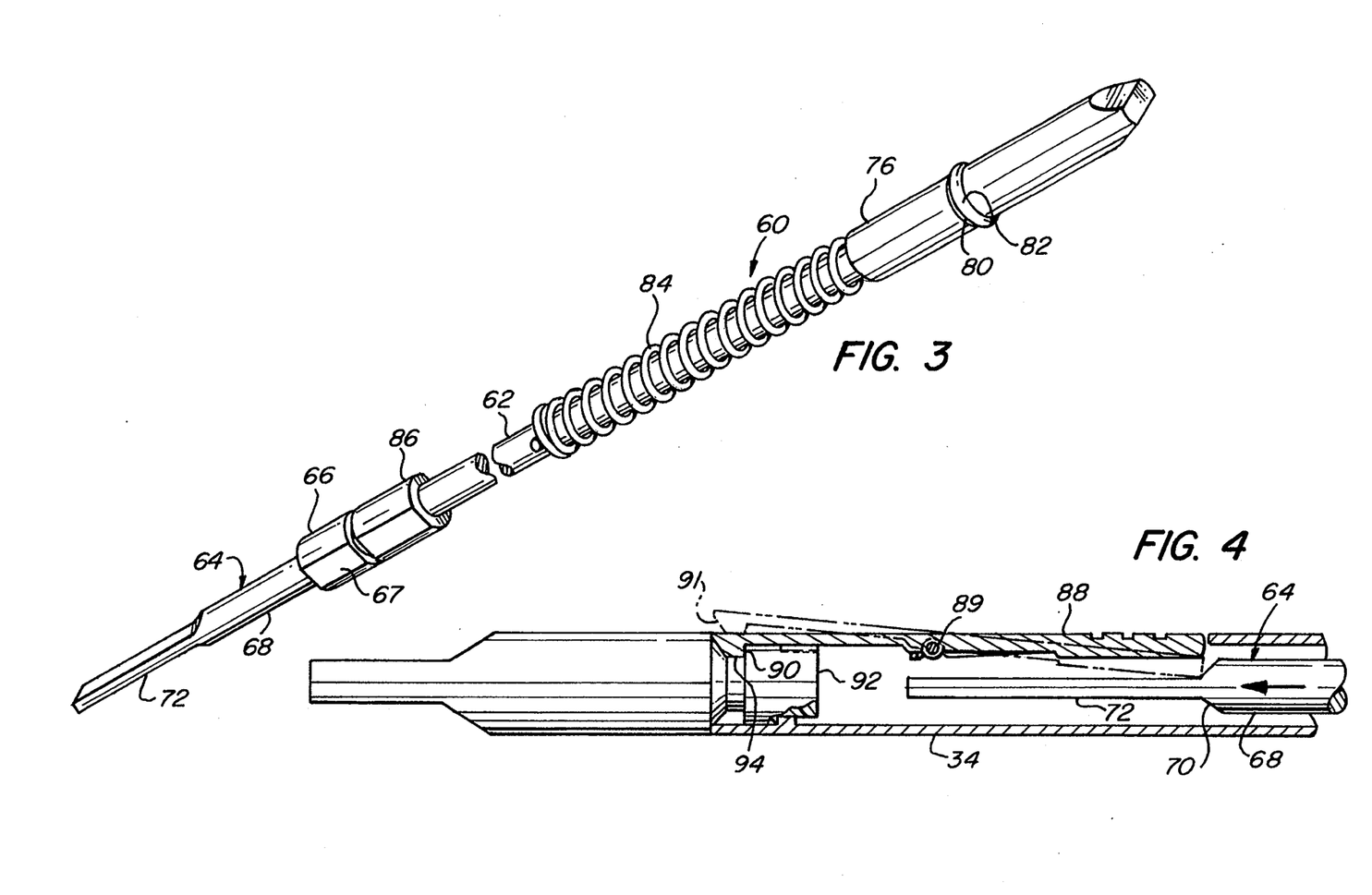
FIG. 3 is a perspective view of an advancing mechanism of the ligation clip applicator.
FIG. 4 is a side elevational view, partly in vertical cross-section, of the ligation clip applicator showing a ligation clip module and the distal end of the neck portion.

FIG. 3 shows a sliding advancing mechanism, or advancer, 61 housed within hollow shaft 34 of the neck portion. The advancer is comprised of a cylindrical advancing shaft 62 connected at its distal end to an actuator 64. As shown in FIGS. 3 and 4, the actuator has a cylindrical section 68, on which a bearing 66 can ride and that tapers to a flat blade-like portion 72 having a rectangular cross-section. The bearing 66 is generally cylindrical but includes at least one flat surface 67 on its outer periphery running its entire axial length. The proximal end of advancing shaft 62 is secured to a cylindrical shaft adapter 76 by a transverse pin 78 as shown in FIG. 5. The diameter of the shaft adapter approximates the inner diameter of hollow shaft 34. The shaft adapter also has a circumferential notch 80 in which resilient O-ring 82 is mounted, for stabilizing axial movement of the advancer within the hollow shaft and to act as a gaseous seal.

The advancer is urged toward the proximal end of the neck portion by a compression return spring 84 and sliding bushing 86. Both the spring and the barrel slide freely on the advancing shaft 62, with the proximal end of the spring abutting shaft adapter 76.

The advancer is assembled in the neck by inserting it in the proximal end of the barrel assembly. As shown in FIG. 5, a short stop pin 87 extends inwardly from the inner surface of hollow shaft 34 in an intermediate region. When the advancer is inserted through the hollow shaft, the flat surface 67 of bearing 66 must oppose the stop pin 87 to permit it to slide past the pin and enable the advancer to be completely inserted into the hollow shaft. However, the sliding bushing 86, by virtue of its being cylindrical, cannot slide past the stop pin, and thus becomes arrested at that position. Further insertion of the advancer causes the spring 84 to engage the shaft adapter 76, thereby biasing the advancer in the rearward direction against the actuating end 19 of the trigger. When the advancer is fully inserted into the neck portion, the end cap 24 is placed on the barrel assembly.

Of course, other means for securing the advancer in the hollow shaft 34 and biasing it in the rearward direction are within the scope of the invention.

As can be seen in FIG. 5, when the trigger 18 is pivoted in the counterclockwise direction about the pivot shaft 20 the top or actuating end 19 of the trigger engages the proximal end of the shaft adapter 76 thereby to urge the advancer assembly forwardly against the biasing force of the spring 84.

The shaft adapter 76, bushing 86 and bearing 66 of the advancer are preferably made of a non-metallic material, such as, for example, a hard plastic or a similar type polymer. In this way, sliding contact between the advancer and the hollow shaft is between non-metallic and metallic parts, thus reducing wear and providing smooth operation of the applicator. Alternatively, a similar result can be obtained using parts coated with a friction reducing material such as titanium nitride.

Figure 6:
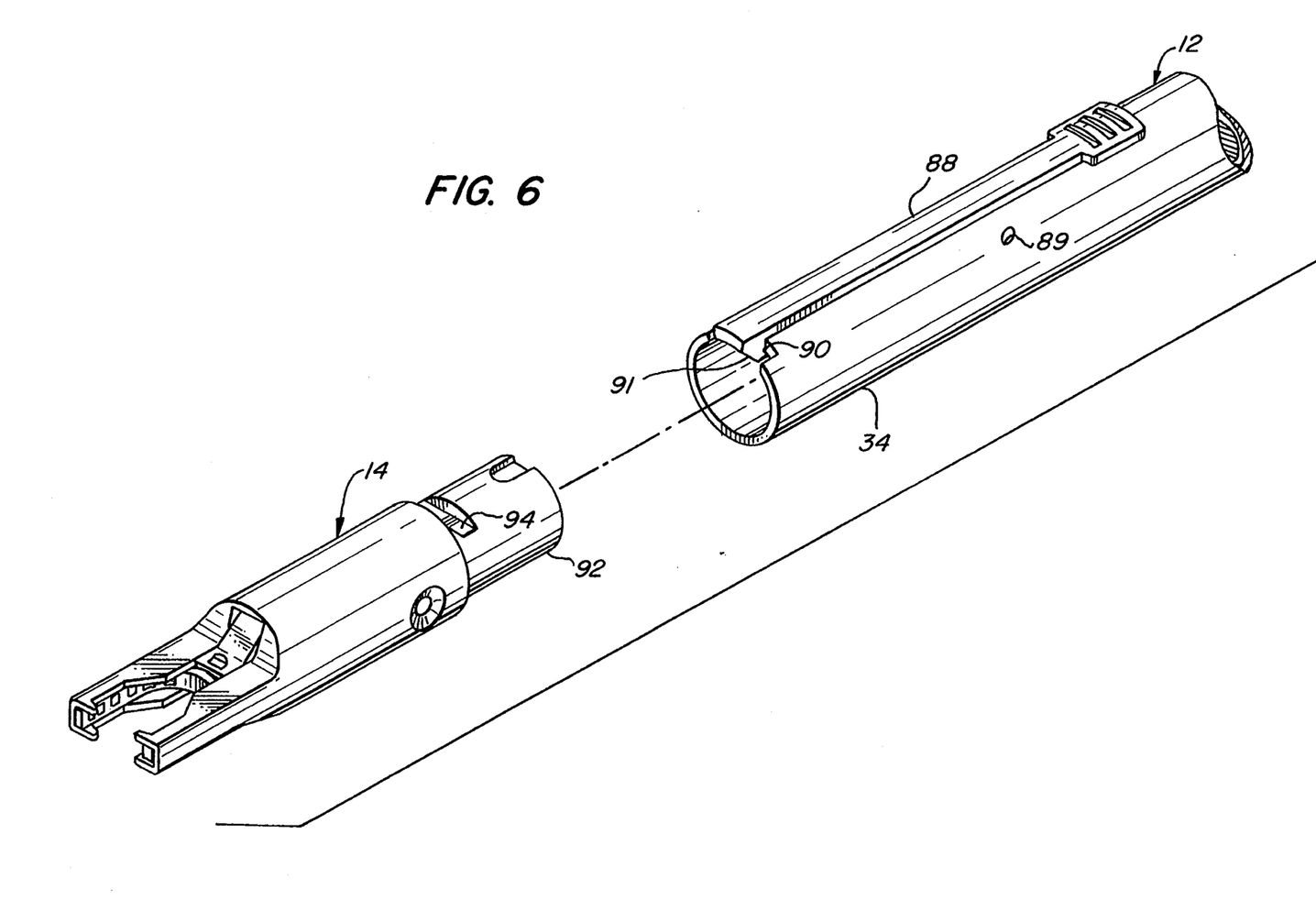
FIG. 6 is a perspective view of the distal end of the ligation clip applicator.

FIGS. 4 and 6 illustrate how the ligation clip module 14 is attached to the distal end of hollow shaft 34. Referring specifically to FIG. 6, a spring-loaded latch 88 is pivotably mounted on a pivot pin 89 carried in a wall of the shaft 34. The distal end of the latch is provided with a pawl 90. The module has a reduced diameter section 92 which fits into the open end of the hollow shaft. To secure the module in the hollow shaft, the proximal end of the latch is pressed down to raise the pawl as shown in phantom lines in FIG. 4. The module is then inserted and the latch is released so the pawl catches a transverse groove 94 in the reduced diameter section to securely lock the module in the neck portion. Advantageously, the pawl 90 of the latch can be provided with a cam surface 91 that rides up on the proximal extreme of the reduced diameter section 92 of the module. In this way, the latch surface 92 of the pawl is automatically guided to the groove 94 when the module is inserted into the neck portion.

As a safety feature, when the latch is pivoted in the open position as shown in FIG. 4, the proximal end of the latch abuts a tapered portion 70 of the actuator and prevents the advancer from moving farther forwardly in the hollow shaft.

Similarly, when the module is properly mounted in the neck portion and the actuator 64 is advanced to apply a ligation clip, as described below, the cylindrical section 68 of the actuator prevents the proximal end of the latch from being depressed to release the module.

Figure 7:
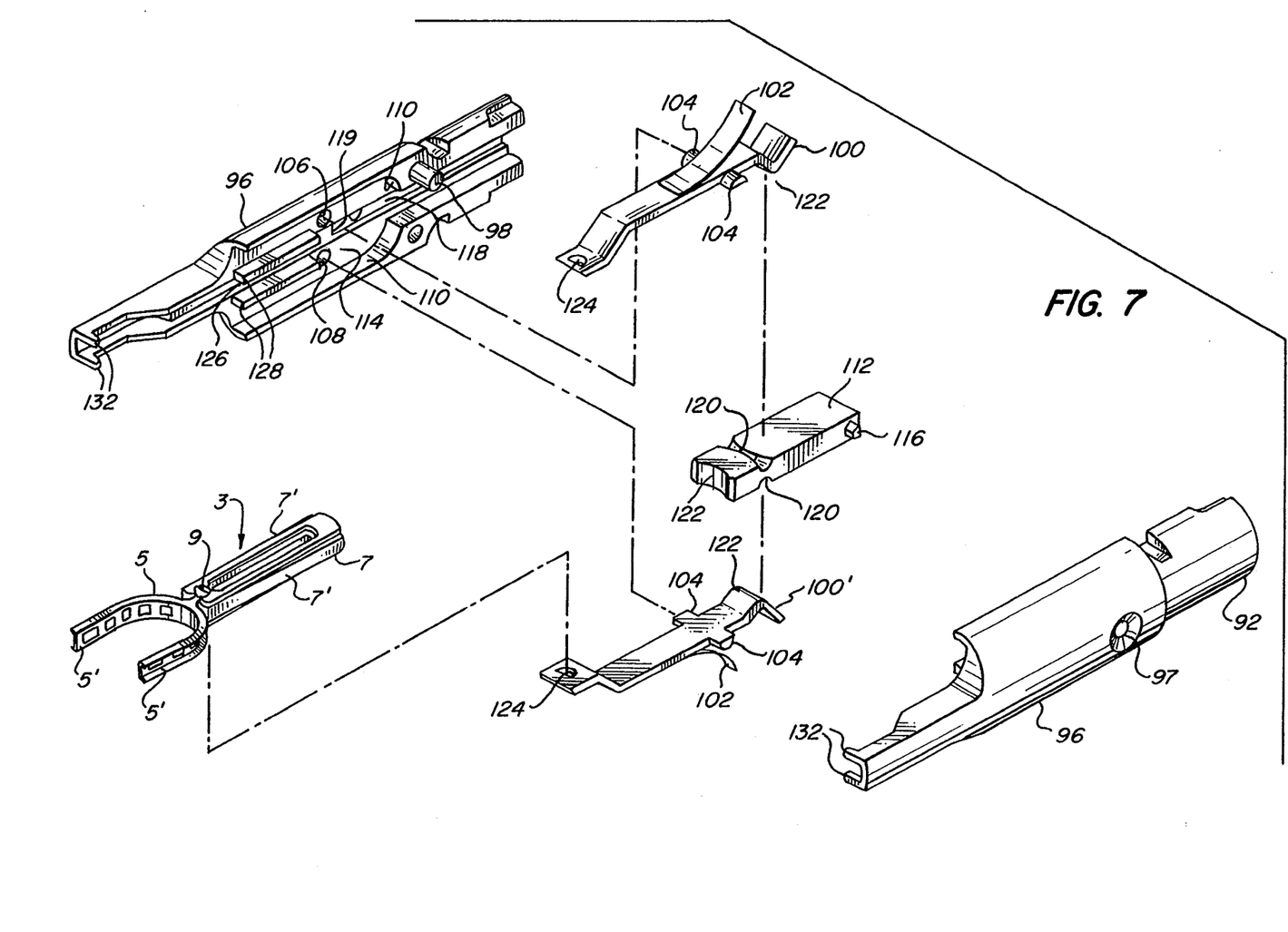
FIG. 7 is an exploded perspective view of the ligation clip module of the ligation clip applicator.

The individual components of the ligation clip module 14 are shown in FIG. 7. The module housing includes two substantially identical cartridge halves 96. The cartridge halves are joined together by inserting an alignment pin 98 in one cartridge half into an unseen alignment hole in the other cartridge half and preferably gluing or otherwise securing the halves together. Upper and lower latches 100 and 100' each have an integral spring 102, and opposing trunions 104 which pivot in holes 106 and 108 in both cartridge halves. The integral springs press against ribs 110 in each cartridge half and urge the proximal ends of the latches toward each other.

A pusher 112 rides in a track 114 provided in the opposing cartridge halves. Laterally extending bosses 116 also align with axial grooves 118 within each cartridge half and act as stops to limit forward movement of the pusher by engaging the distal extremes 119 of the grooves 118. Nevertheless, the bosses 116 are designed to shear off to permit the clip to be forced out of the module after it is closed if the clip does not otherwise release from the module. The pusher includes a pair of transverse slots 120, one on each of its sides, for receiving a V-shaped bend 122 in each latch 100, 100'. In the rest or unfired position of the cartridge, the proximal ends of the latches 100, 100' are spaced apart by the pusher with the V-shaped bends received in the slots 120, thereby to hold the distal ends of the latches relatively close together. In addition, the front of the pusher has a curved portion 122 with a radius to match the rear end of the ligation clip as will be described below.

A window 97 in each cartridge half allows the user to view the pusher when it is in the pre-actuated, or ready-to-fire, position.

While the latches are preferably made of metal, the other parts of the module can be formed of plastic or other similar material. As will also be appreciated, the module is disposable. In addition, different size modules for mounting various size ligation clips can be easily connected to the same hollow shaft by using a standard size reduced diameter section.

The ligation clip 3, which is of the type described in U.S. Pat. No. 4,590,937 and more specifically in U.S. patent application Ser. No. 07/906,938 can be seen in FIG. 7 to include a Y-shaped clamp 5 and a U-shaped clip body 7. As explained in detail in that application, the clip is closed by drawing the clamp 5 into the body 7 so that the legs 7' of the body urge the arms 5' of the clamp together. The clip body slides into and be secured within a raceway 126 within the cartridge. The raceway is defined by straight ribs 128 on both cartridge halves. Posts 9 extend from the Y-shaped clamp and are shaped to engage in holes 124 formed in the distal ends of the latches 100, 100'.

Figure 8:
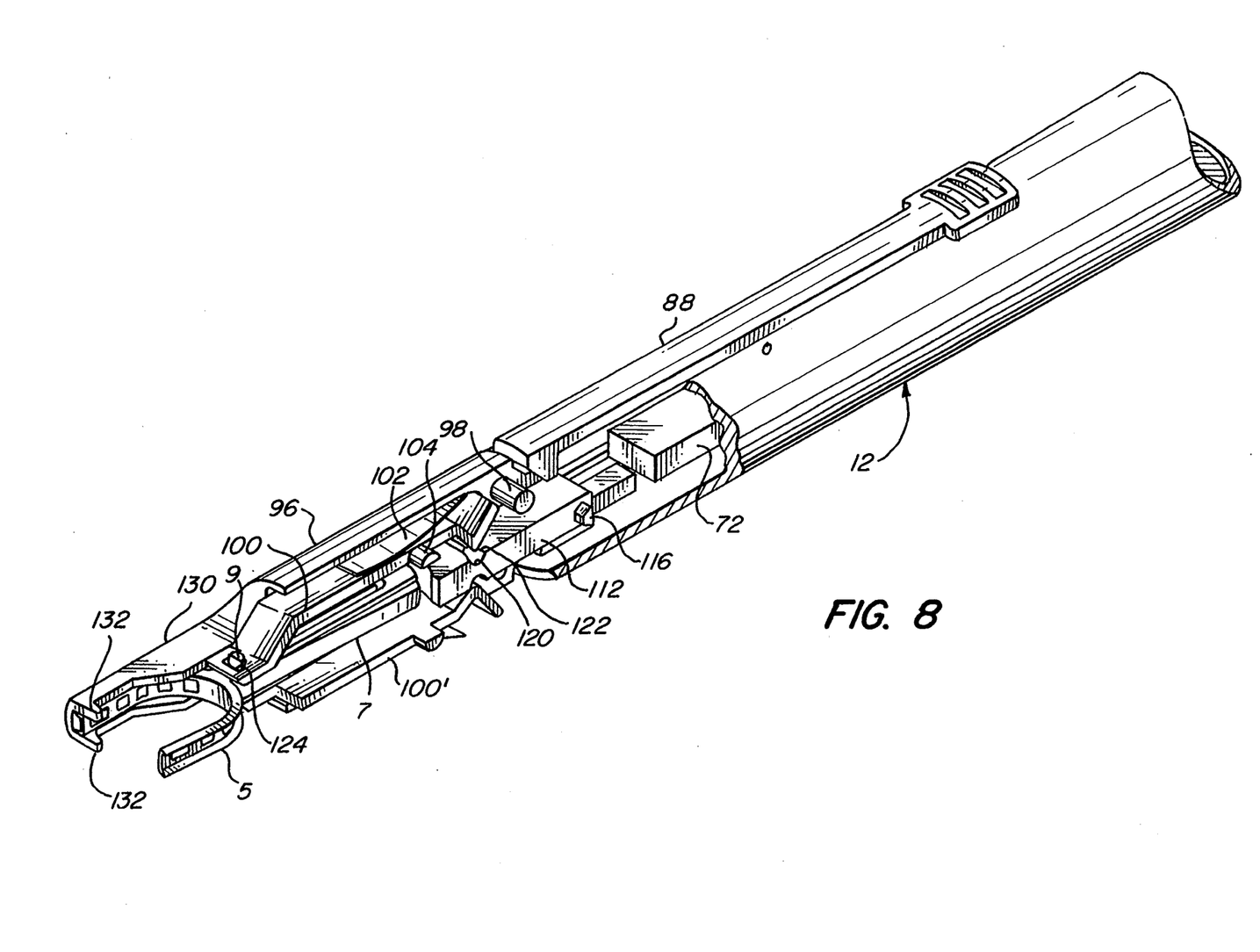
FIG. 8 is a perspective view of the distal end of the ligation clip applicator showing the ligation clip loaded in the ligation clip module and ready to be fired.

FIG. 8 shows the ligation clip loaded in the ligation clip applicator and ready to be fired. In this attitude, the clip body 7 is positioned within the raceway and the Y-shaped clamp is protected within opposing flanges 130 and extended tips or hooks 132 of the cartridge halves 96 only one of each of which is shown in FIG. 8. The opposed hooks of the assembled cartridge halves can be used to manipulate tissue when positioning a clip about a vessel to be ligated. The clamp is also held stationary by the posts 9 which are engaged in holes 124 in the latches. The pusher 112 is positioned behind the clip body and will slide forwardly upon actuation by the flat portion 72 of the advancer.

With the applicator loaded with a module holding the ligation clip and ready to be fired, the ligation clip may be positioned around the vessel to be ligated. Because of the slender and elongated design of the neck portion, the ligation clip applicator is ideally suited for use in minimally invasive surgical techniques. For example, the applicator can be used with such techniques by inserting the ligation clip carried in the clip module and the attached neck portion through a cannula in the patient to where the vessel to be ligated is located. The O-ring 82, which seals between the shaft 34 and the advancer assembly, acts as an internal gaseous sealing means for the applicator in such procedures.

Figure 9:
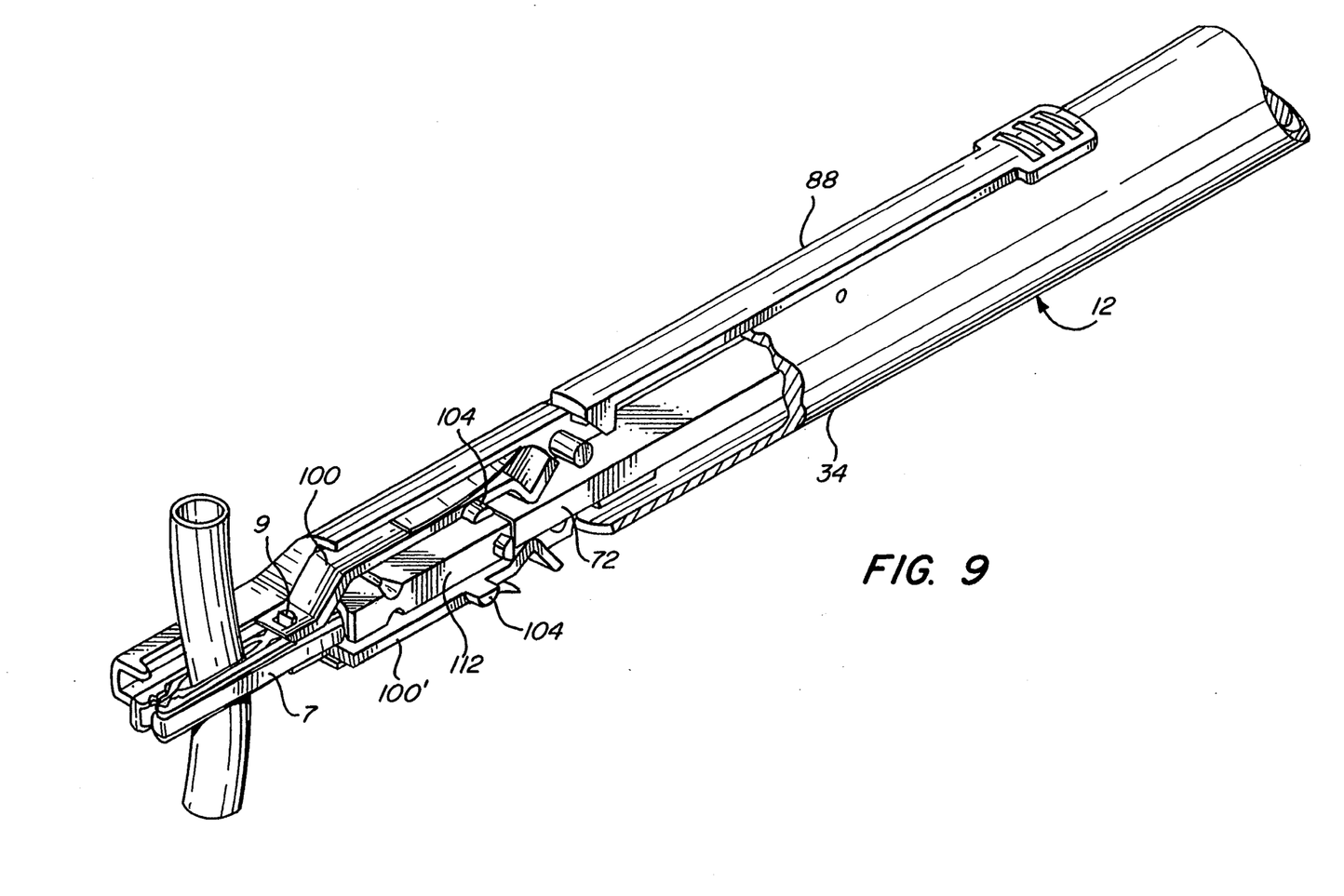
FIG. 9 is a perspective view of the distal end of the ligation clip applicator showing the advancing mechanism in the actuated position and the ligation clip closed around the vessel.

In FIG. 9, the ligation clip is shown in position around the vessel to be ligated after the trigger 18 has been squeezed to slide the advancer, and through their mutual abutment, the pusher forwardly in a firing stroke. The flat portion 72 of the advancer forces the pusher in the forward direction, which in turn advances the clip body 7 forwardly to engage and compress the Y-shaped clamp, which is held in a fixed position by engagement of the latches, around the vessel. In this position, the bosses 116 of the pusher are visible in windows 97 of the cartridge housing, confirming that the ligation clip has been fired. As can be seen in FIG. 9, the flat portion 72 of the advancer assumes the position of the pusher between the V-shaped bends in the latches 100, 100' to hold their distal ends together, to continue to secure the Y-shaped clamp of the ligation clip in its fixed position.

Figure 10:
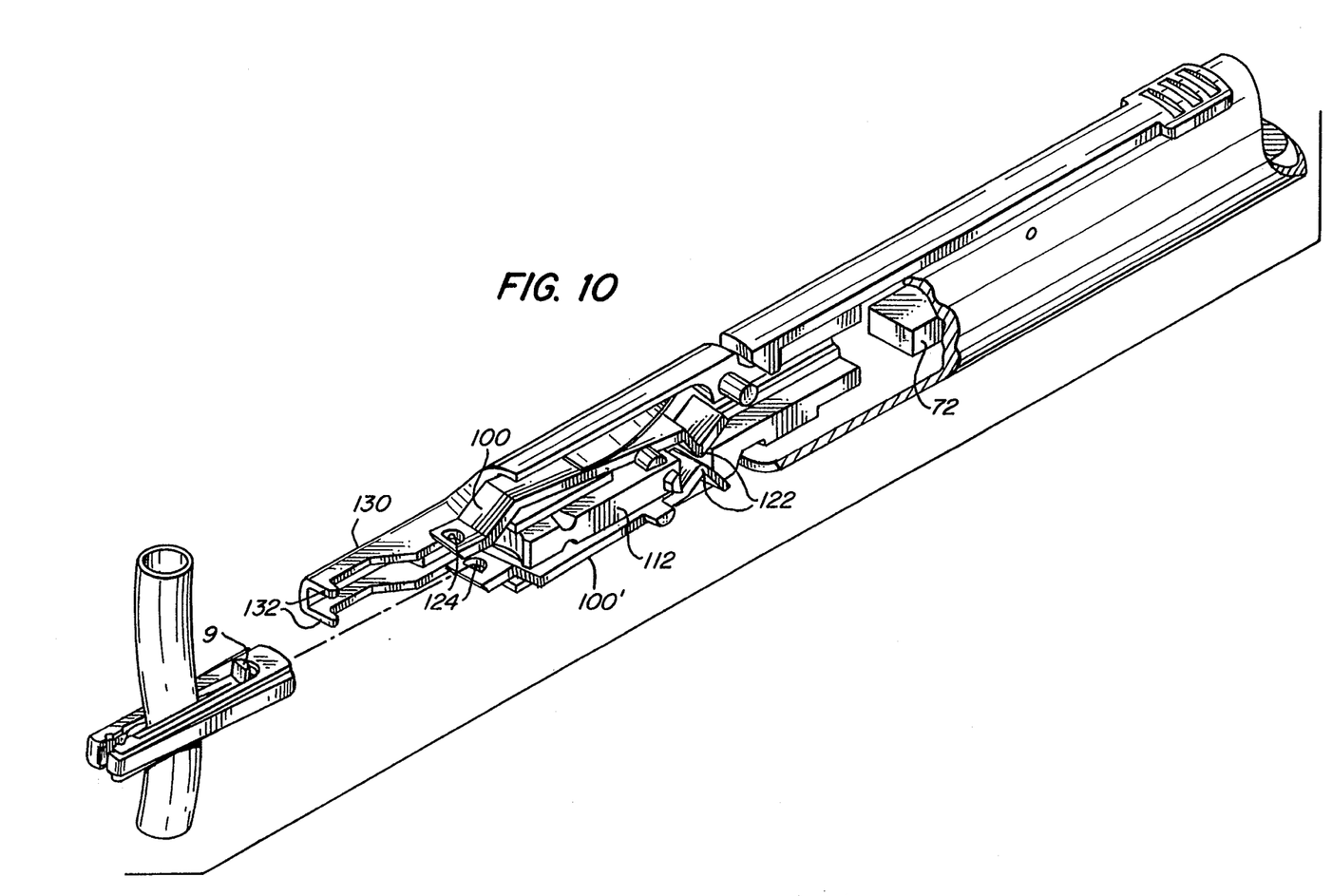
FIG. 10 is a perspective view of the distal end of the ligation clip applicator showing the advancing mechanism in the retracted position and the ligation clip closed about a vessel and released from the ligation clip module.

When the trigger is released, the advancer retreats in a return stroke in the rearward direction due to the biasing force of compression spring 84. However, as shown in FIG. 10, this action leaves the pusher in the forward position in the cartridge, and therefore no obstruction is provided opposite to the V-shaped bends 122 in the latches. As a result, the biasing force of the integral springs collapses the latches together at their proximal ends. The distal ends of the latches thus separate and release engagement with the posts 9 of the Y-shaped clamp. The ligation clip can then freely slide out of the module. The fired module can thereafter be released from the hollow shaft by pivoting the latch 88 and removing it from the hollow neck shaft 12 to be discarded. A new module can then be inserted and secured in the hollow shaft and the applicator is then ready to be used again.

Accordingly, the present invention provides a unique and novel device for reliably and efficiently applying two-part ligation clips to vessels to be ligated.

Although a specific embodiment of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A module for mounting a two-part ligation clip having a first part formed to be closed about a vessel and a second part movable relative to the first part to cause the first part to close, said module being operable in conjunction with a ligation clip applicator and comprising:
   a cartridge housing;
   holding means, mounted in said cartridge housing, for holding the first part of the ligation clip in a stationary position relative to said housing; and
   sliding means, mounted for advancing movement in said cartridge housing, for advancing the second part of the ligation clip relative to the first part to close the first part, wherein
   said sliding means includes a pusher axially slidable in said housing, and said latch includes a spring for biasing said latches against said pusher, said pusher holding said latches in position to grip the first part of the ligation clip.

2. A module according to claim 1, wherein said holding means comprises a pair of latches pivotably mounted in said housing.

3. A module according to claim 1, further comprising means for indicating when said pusher has been advanced.

4. A ligation clip applicator according to claim 1, wherein said cartridge housing is formed with opposing flange means for embracing at least a portion of the first part of the ligation clip, said flange means terminating in opposing inwardly directed hook means for manipulating tissue to be ligated.

5. A ligation clip applicator for applying a two-part ligation clip to a vessel, the ligation clip including a first part formed to be closed about a vessel and a second part movable relative to the first part to cause the first part to close; said applicator comprising:
   a handle assembly having a squeezable, pivotably mounted trigger;
   an elongated shaft connected at its proximal end to said handle assembly;
   a sliding advancer mounted in said shaft for reciprocal movement therein, said trigger being mounted to move said advancer axially in a forward direction when squeezed; and
   a module, mountable at a distal end of said elongated shaft, for supporting the ligation clip, said module having a cartridge housing, at least one latch pivotably mounted in said housing for holding the first part of the ligation clip in a stationary position relative to said actuator, and a sliding pusher slidable within said housing upon actuation of said advancer for engaging and advancing the second part of the ligation clip relative to the first part to close the first part, wherein
   two said latches are mounted in said housing, and each latch includes a spring for biasing said latch against said pusher, said pusher holding said latches in position to grip the first part of the ligation clip.

6. A ligation clip applicator according to claim 5, wherein said module includes means for indicating when said pusher has been advanced.

7. A ligation clip applicator for applying a two-part ligation clip to a vessel, the ligation clip including a first part formed to be closed about a vessel and a second part movable relative to the first part to cause the first part to close; said applicator comprising:
   an elongated hollow shaft;
   a sliding advancer mounted for reciprocal movement in said shaft;
   a handle assembly connected to a proximal end of said shaft and including actuating means for advancing said sliding advancer; and
   a module mountable on a distal end of said shaft, said module including holding means for holding the first part of the ligation clip in a stationary position relative to said applicator, and sliding means operable by said sliding advancer for engaging and advancing the second part of the ligation clip relative to the first part to close the first part, wherein
   said holding means comprises a pair of latches housed in said module for gripping the first part of the ligation clip; wherein said sliding means comprises a pusher slidable axially within said module upon actuation by said actuating means; and wherein said module further comprises latch biasing means for biasing said pair of latches against said pusher, said pusher holding said latches in position to grip the first part of the ligation clip.

8. A ligation clip applicator for applying a two-part ligation clip to a vessel, the ligation clip including a first part formed to be closed about a vessel and a second part movable relative to the first part to cause the first part to close; said applicator comprising:

a module for supporting the two-part ligation clip, said module including holding means for holding the first part of the ligation clip in a stationary position relative to said applicator, and sliding means for engaging and advancing the second part of the ligation clip relative to the first part to close the first part;

actuating means, mountable with said module, for actuating said sliding means, wherein said holding means comprises a pair of latches housed in said module for gripping the first part of the ligation clip; wherein said sliding means comprises a pusher slidable axially within said module upon actuation by said actuating means; and wherein said module further comprises latch biasing means for biasing said pair of latches against said pusher, said pusher holding said latches in position to grip the first part of the ligation clip.

9. A ligation clip applicator for applying a two-part ligation clip to a vessel, the ligation clip including a first part formed to be closed about a vessel and a second part movable relative to the first part to cause the first part to close; said applicator comprising:

an elongated hollow shaft;

a sliding advancer mounted for reciprocal movement in said shaft;

a handle assembly connected to a proximal end of said shaft and including actuating means for advancing said sliding advancer; and a module mountable on a distal end of said shaft, said module including holding means for holding the first part of the ligation clip in a stationary position relative to said applicator, and sliding means operable by said sliding advancer for engaging and advancing the second part of the ligation clip relative to the first part to close the first part, wherein said holding means comprises a pair of latches housed in said module for gripping the first part of the ligation clip and the first part of the ligation clip has at least one transversely projecting post and wherein at least one of said latches is formed with a hole for receiving the post thereby to provide the gripping action.

10. A module for mounting a two-part ligation clip having a first part formed to be closed about a vessel and a second part movable relative to the first part to cause the first part to close, said module being operable in conjunction with a ligation clip applicator and comprising:

a cartridge housing;

holding means, mounted in said cartridge housing, for holding the first part of the ligation clip in a stationary position relative to said housing; and sliding means, mounted for advancing movement in said cartridge housing, for advancing the second part of the ligation clip relative to the first part to close the first part, wherein the first part of the ligation clip has at least one transversely projecting post and wherein at least one of said latches is formed with a hole for receiving the post thereby to provide said holding action.

11. A ligation clip applicator for applying a two-part ligation clip to a vessel, the ligation clip including a first part formed to be closed about a vessel and a second part movable relative to the first part to cause the first part to close; said applicator comprising:

a module for supporting the two-part ligation clip, said module including holding means for holding the first part of the ligation clip in a stationary position relative to said applicator, and sliding means for engaging and advancing the second part of the ligation clip relative to the first part to close the first part;

actuating means, mountable with said module, for actuating said sliding means, wherein said holding means comprises a pair of latches housed in said module for gripping the first part of the ligation clip, and the first part of the ligation clip has at least one transversely projecting post and wherein at least one of said latches is formed with a hole for receiving the post thereby to provide said gripping action.

12. The ligation clip applicator according to claim 11, wherein said module is formed with opposing flange means for embracing at least a portion of the first part of said ligation clip, said flange means terminating in opposing inwardly directed hook means for manipulating tissue to be ligated.

13. A ligation clip applicator for applying a two-part ligation clip to a vessel, the ligation clip including a first part formed to be closed about a vessel and a second part movable relative to the first part to cause the first part to close; said applicator comprising:

a module for supporting the two-part ligation clip, said module including holding means for holding the first part of the ligation clip in a stationary position relative to said applicator, and sliding means for engaging and advancing the second part of the ligation clip relative to the first part to close the first part;

actuating means, mountable with said module, for actuating said sliding means, wherein said actuating means comprises a handle assembly including a pivotally mounted trigger and a neck portion, said neck portion including a hollow shaft and a sliding advancer slidably mounted in said shaft, said trigger being associated with said advancer to drive said advancer in a forward direction to actuate said sliding means when said trigger is pivoted; and a connecting latch pivotally mounted in the region of the distal end of said hollow shaft, said latch being formed to engage said module in a closed position, and in an open position to abut said advancer and prevent it from sliding in the forward direction.

14. A ligation clip applicator for applying a two-part ligation clip to a vessel, the ligation clip including a first part formed to be closed about a vessel and a second part movable relative to the first part to cause the first part to close; said applicator comprising:

a module for supporting the two-part ligation clip, said module including holding means for holding the first part of the ligation clip in a stationary position relative to said applicator, and sliding means for engaging and advancing the second part of the ligation clip relative to the first part to close the first part;

actuating means, mountable with said module, for actuating said sliding means, wherein said actuating means comprises a handle assembly including a pivotally mounted trigger and a neck portion, said neck portion including a hollow shaft and a sliding advancer slidably mounted in said shaft, said trigger being associated with said advancer to drive said advancer in a forward direction to actuate said sliding means when said trigger is pivoted; and a connecting latch pivotally mounted in the region of the distal end of said hollow shaft, said latch being configured to engage said module in a closed position, said latch further being configured to be engaged in the closed position by said advancer, when said advancer is moved in the forward direction, thereby to prevent said latch from moving from the closed position.

15. A ligation clip applicator for applying a two-part ligation clip to a vessel, the ligation clip including a first part formed to be closed about a vessel and a second part movable relative to the first part to cause the first part to close; said applicator comprising:

an elongated hollow shaft;

a sliding advancer mounted for reciprocal movement in said shaft;

a handle assembly connected to a proximal end of said shaft and including actuating means for advancing said sliding advancer; and a module mountable on a distal end of said shaft, said module including holding means for holding the first part of the ligation clip in a stationary position relative to said applicator, and sliding means operable by said sliding advancer for engaging and advancing the second part of the ligation clip relative to the first part to close the first part, wherein said advancer comprises an advancing shaft having a shaft adapter at its proximal end and biasing means for biasing said advancer in a rearward direction toward said handle assembly, and said biasing means includes a compression spring and a cylindrical bushing, both freely slidable on said advancing shaft, and abutment means in said hollow shaft for blocking axial movement of said bushing in a forward direction.

16. A ligation clip applicator according to claim 15, wherein said advancer further comprises an actuator and a bearing connecting said actuator to a distal end of said advancing shaft, wherein said bearing is shaped to avoid said abutment means and is slidable in the axial direction.

17. A ligation clip applicator according to claim 15, wherein said actuating means includes a squeezable trigger attached to said handle assembly for movement relative thereto.

18. A ligation clip applicator according to claim 15, wherein said sliding means comprises a pusher slidable axially to advance within said module upon actuation by said advancer.

19. A ligation clip applicator according to claim 18, wherein said module includes means for indicating when said pusher has been advanced.

20. A ligation clip applicator for applying a two-part ligation clip to a vessel, the ligation clip including a first part formed to be closed about a vessel and a second part movable relative to the first part to cause the first part to close; said applicator comprising:

a module for supporting the two-part ligation clip, said module including holding means for holding the first part of the ligation clip in a stationary position relative to said applicator, and sliding means for engaging and advancing the second part of the ligation clip relative to the first part to close the first part;

actuating means, mountable with said module, for actuating said sliding means, wherein said actuating means comprises a handle assembly including a pivotally mounted trigger and a neck portion, said neck portion including a hollow shaft and a sliding advancer slidably mounted in said shaft, said trigger being associated with said advancer to drive said advancer in a forward direction to actuate said sliding means when said trigger is pivoted; and connecting means for rotatably connecting said neck portion to said handle assembly.

21. A ligation clip applicator according to claim 11, wherein said sliding means comprises a pusher slidable axially to advance within said module upon actuation by said actuating means.

22. A ligation clip applicator according to claim 21, wherein said module includes means for indicating when said pusher has been advanced.

23. A ligation clip applicator according to claim 20, further comprising advancer biasing means for biasing said advancer in a rearward direction.

* * * * *